United States Patent [19]

Töpfl

[11] Patent Number: 5,232,628
[45] Date of Patent: Aug. 3, 1993

[54] POLYADDUCTS OF ALKYLENE OXIDE AND STYRENE OXIDE WITH ARYL ALKANOLS

[75] Inventor: Rosemarie Töpfl, Dornach, Switzerland

[73] Assignee: Ciba-Geigy Corporation, Ardsley, N.Y.

[21] Appl. No.: 866,647

[22] Filed: Apr. 8, 1992

Related U.S. Application Data

[62] Division of Ser. No. 585,746, Sep. 20, 1990, Pat. No. 5,126,474.

[30] Foreign Application Priority Data

Sep. 27, 1989 [CH] Switzerland .................... 3496/89

[51] Int. Cl.$^5$ ..................... B01F 17/06; B01F 17/12
[52] U.S. Cl. ..................... 252/354; 252/351; 252/356; 252/8.9
[58] Field of Search ............. 252/351, 354, 356, 8.9

[56] References Cited

U.S. PATENT DOCUMENTS

| | | | |
|---|---|---|---|
| 2,213,139 | 8/1940 | Huttenlocher | 252/351 X |
| 2,888,489 | 5/1959 | Horsley | 568/609 |
| 4,648,984 | 3/1987 | Krause et al. | 252/351 X |
| 4,703,114 | 10/1987 | Mori et al. | 536/41 |
| 4,713,482 | 12/1987 | Topfl | 560/196 |
| 4,894,183 | 1/1990 | Topfl | 252/358 |
| 5,126,476 | 6/1992 | Töpfl | 558/34 |

*Primary Examiner*—Robert L. Stoll
*Assistant Examiner*—Daniel S. Metzmaier
*Attorney, Agent, or Firm*—Marla J. Mathias; George R. Dohmann

[57] ABSTRACT

Polyadducts of an alkylene oxide and styrene oxide with an aryl alcohol, especially polyadducts of formulae

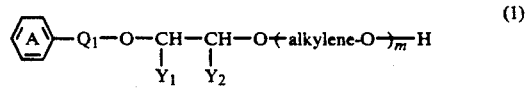

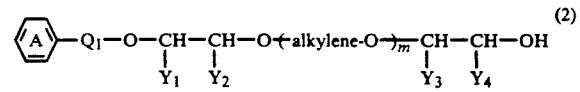

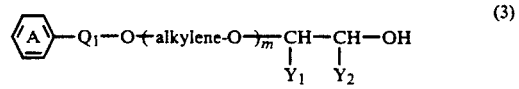

wherein the ring A is an unsubstituted phenyl radical or a phenyl radical which is substituted by halogen, methyl or $C_1$–$C_3$alkoxy, $Q_1$ is alkylene of 1 to 4 1 carbon atoms, preferably methylene, in the pairs of substituents ($Y_1$ and $Y_2$) and ($Y_3$ and $Y_4$) one Y is phenyl and the other Y is hydrogen, "alkylene" denotes an alkylene radical of 2 or 3 carbon atoms, and m is an integer from 1 to 80.

These polyadducts are a novel class of nonionic or anionic surfactants which are used as textile auxiliaries.

2 Claims, No Drawings

POLYADDUCTS OF ALKYLENE OXIDE AND STYRENE OXIDE WITH ARYL ALKANOLS

This is a divisional of Ser. No. 585,746, filed Sep. 20, 1990, now U.S. Pat. No. 5,126,474, issued Jun. 30, 1992.

The present invention relates to polyadducts of alkylene oxide and styrene oxide with aryl alkanols and to the use thereof, preferably as emulsifiers, dyeing auxiliaries and, most preferably, as wetting agents or padding auxiliaries.

The polyadducts of this invention are obtained by addition of an alkylene oxide and styrene oxide to an aryl alkanol and are also prepared in the form of their acid esters and salts thereof.

The addition may be carried out in any order using 1 to 100 mol of alkylene oxide and 1 or 2 mol of styrene oxide.

The aryl alkanol used may be benzyl alcohol, α-methylbenzyl alcohol, 2-phenylethanol or phenyl isopropanol. Benzyl alcohol is preferred.

The alkylene oxide may suitably be ethylene oxide, propylene oxide or butylene oxide.

Preferred polyadducts are those of formula

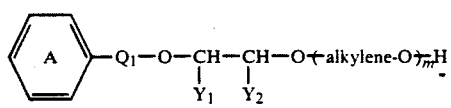

and their acid esters and salts thereof.

Further polyadducts are those of formulae

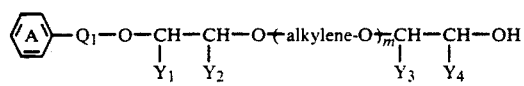

and

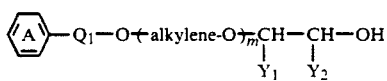

These polyadducts of formulae (2) and (3) may also be obtained in the form of their acid esters and salts thereof.

In formulae (1), (2) and (3) the ring A is an unsubstituted phenyl radical or a phenyl radical which is substituted by halogen, methyl or $C_1$-$C_3$alkoxy such as isopropoxy and, preferably, methoxy.

$Q_1$ is alkylene of 1 to 4 carbon atoms, preferably ethylene or, most preferably, methylene.

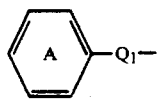

is conveniently the hydrocarbon radical of an aromatic-aliphatic alcohol of 7 to 9 carbon atoms. Preferably

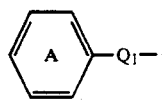

is the benzyl radical.

Araliphatic alcohols may suitably be benzyl alcohol, phenyl ethanol, methylphenyl ethanol, chlorophenyl ethanol or phenyl isopropanol.

"Alkylene" denotes an alkylene radical of 2 or 3 carbon atoms such as ethylene or propylene or a combination thereof. m is an integer from 1 to 80, preferably from 2 to 40 and most preferably from 2 to 10.

(Alkylene—O)-chains are preferably of the ethylene glycol, propylene ethylene glycol or ethylene propylene glycol type. The first mentioned type is especially preferred.

In the pairs of substituents ($Y_1$ and $Y_2$) and ($Y_3$ and $Y_4$) one Y is phenyl and the other Y is hydrogen. Preferably $Y_1$ and $Y_3$ are phenyl and $Y_2$ and $Y_4$ are hydrogen.

The polyadducts of formula (1) are prepared by first etherifying the aromatic-aliphatic alcohol with 1 mol of styrene oxide, followed by the addition of 1 to 80 mol of alkylene oxide (ethylene oxide and/or propylene oxide) to the reaction product.

The etherification of the aromatic-aliphatic alcohol with styrene oxide is conveniently carried out in almost anhydrous or substantially non-aqueous medium in the temperature range from 40° to 90° C., under normal pressure or under pressure, and in the presence of boron trifluoride etherate.

The addition of the alkylene oxide to the substituted phenyl ethanol is carried out by methods which are known per se, using ethylene oxide or propylene oyxide or, alternatively, ethylene oxide and propylene oxide or a mixture of ethylene oxide and propylene oxide. The adducts of formula (2) are prepared by terminally etherifying the adducts of formula (1) with a further 1 mol of styrene oxide.

The polyadducts of formula (3) are prepared by first etherifing the aromatic-aliphatic alcohol with 1 to 80 mol of alkylene oxide (ethylene oxide and/or propylene oxide), followed by the addition of 1 mol of styrene oxide to the resultant polyalkylene glycol ether.

The etherification of the aromatic-aliphatic alcohol as well as the terminal addition of styrene oxide can be carried out in accordance with the above mentioned conditions.

Depending on the acid radical, the acid esters can be obtained in the form of monoesters, diesters or hemiesters and as free acids, or preferably as salts, for example alkali metal salts or alkaline earth metal salts or ammonium salts. Alkali metal salts are preferably the sodium, potassium or lithium salts; and alkaline earth metal salts are typically the magnesium and calcium salts; while ammonium salts are the ammonium, dimethylammonium, trimethylammonium, monoethanolammonium, diethanolammonium and triethanolammonium salts. The acid esters are preferably prepared as ammonium salts. Mono- or diethanolammonium salts can be further etherified with 1 to 4 oxyethylene units.

The acid esters are prepared by reacting the nonionic polyadduct of, for example, formula (1), (2) or (3) with an at least dibasic oxyacid and, if desired, converting the resultant acid ester into an above-mentioned salt.

Suitable polybasic oxyacids for forming the acid esters are sulfonated or unsulfonated organic, preferably aliphatic, dicarboxylic acids of 3 to 6 carbon atoms, for example maleic acid, malonic acid, succinic acid or sulfosuccinic acid, and polybasic inorganic oxyacids such as sulfuric acid or orthophosphoric acid. In place of the acids it is also possible to use their functional derivatives such as acid anhydrides, halides or amides.

Exemplary of these functional derivatives are maleic anhydride, phosphorus pentoxide, chlorosulfonic acid and sulfamic acid. The phosphoric esters are conveniently obtained as mixtures of a monoester and diester.

The esterification is normally carried out by simply mixing the reactants and heating, conveniently to a temperature in the range from 50° to 100° C. The free acids which are initially formed can subsequently be converted into the corresponding alkali metal or ammonium salts. The conversion into the salts is carried out in conventional manner by the addition of a base, for example ammonia, monoethanolamine, triethanolamine or an alkali metal hydroxide, for example sodium hydroxide or potassium hydroxide. Im a particularly preferred embodiment, sulfuric acid monoesters are prepared direct in the form of their ammonium salts by heating the nonionic styrene oxide polyadducts with sulfamic acid, conveniently in the presence of urea.

Useful polyadducts are those of formula

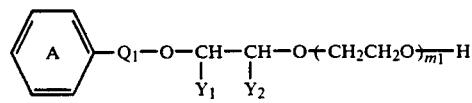
(4)

wherein one of $Y_1$ and $Y_2$ is phenyl and the other is hydrogen and $m_1$ is 2 to 40, preferably 2 to 10.

Preferred acid esters prepared with an inorganic or organic acid are those of formula

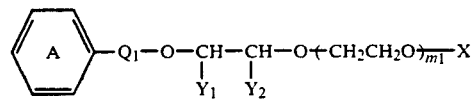
(5)

or those of formula

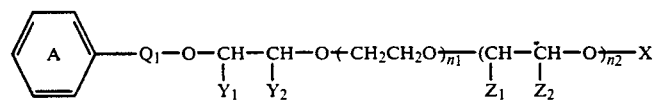
(6)

or those of formula

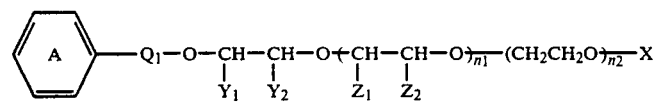
(7)

wherein $Y_1$, $Y_2$ and $m_1$ have the given meanings, one of $Z_1$ and $Z_2$ is methyl and the other is hydrogen, X is the radical of maleic acid, sulfosuccinic acid, sulfuric acid or phosphoric acid, and the sum of $n_1+n_2$ is 2 to 30, preferably 4 to 18.

Preferred acid esters of the formulae (5), (6) and (7) contain either a maleic acid ester group or a sulfuric acid ester group, which are each preferably present in the form of their alkali metal salts or ammonium salts.

Of particular interest are the phosphated polyadducts of formula (4), the phosphate esters being conveniently obtained as mixtures of the corresponding salts of a mono-and diester.

The polyadducts of this invention are suitable for a wide range of uses in textile application, such as pretreatment, dyeing or finishing. Nonionic unesterified products preferably find utility as assistants for dyeing polyamide-containing fibre materials with anionic dyes or dye mixtures. The corresponding acid esters, in particular the dicarboxylic acid hemiesters, sulfuric acid esters and, preferably, phosphoric acid esters, are used primarily as wetting agents, deaerating agents and foam suppressants in aqueous systems, in particular for dyeing natural or synthetic fibre material, preferably for dyeing cellulosic textile materials, polyester fibres or natural or synthetic polyamide fibre materials. Both as nonionic polyadducts and as acid esters, the styrene oxide polyadducts of this invention, in the described formulations, improve the affinity of the dyes and thereby speed up the diffusion of the dyes into the fibres.

The present invention accordingly also provides a process for finishing natural or synthetic fibre material, with or without appropriate dyes, which finishing is carried out in the presence of the nonionic and/or anionic polyadducts of this invention.

The amounts in which the polyadducts are added to the finishing liquors, such as dye liquors or pretreatment or aftertreatment liquors, vary with the substrate, conveniently from 0.5 to 20 g, preferably from 1 to 10 g, per liter of liquor.

Useful formulations contain the polyadducts of this invention as nonionic and/or anionic compounds, with or without water, in conjunction with nonionic or anionic dispersants, fatty alcohols, fatty acid amides, alkylenebis fatty acid amides, alkyl alkenyldicarboxylates, metal stearates, silicone oils, for example dialkylpolysiloxanes, or also mineral oils or alkanolamines in stable, wetting and/or defoaming compositions. Such formulations are also capable of almost completely deaerating aqueous systems. It is thus possible to avoid entrapped air not only in the application baths but also in the substrates. Such deaeration makes it possible to avoid spotting in dyeing and finishing.

Preferred aqueous or non-aqueous formulations are those which, based on the entire formulation, comprise (A) 2 to 50% by weight of an acid ester of the polyadduct of formula (1) or (4), (B) 5 to 50% by weight of a nonionic surfactant, preferably an aliphatic monoalcohol of 6 to 22 carbon atoms, or of the polyadduct of 2 to 80 mol of ethylene oxide with 1 mol of an aliphatic monoalcohol of 6 to 22 carbon atoms or of a polyoxyethylene derivative of a sorbitan fatty acid ester or of a polyadduct of formula (1) or (4) or a mixture thereof and at least one of the following components:

(C) 1 to 30% by weight of a silicone oil, for example a dialkylpolysiloxane such as dimethylpolysiloxane, (D) 10 to 60% by weight of a mineral oil, for example a paraffin oil such as Shell oil L 6189 or a mineral oil Esso 301 to 312, (E) 20 to 45% by weight of a dialkyl ester of an ethylenically unsaturated aliphatic dicarboxylic acid, for example bis-2-ethylhexyl maleate or bis-2-ethylhexyl citraconate, (F) 10 to 70% by weight of a diffusion accelerant, in particular an aliphatic or aromatic carboxylic ester such as alkyl lactate, alkyl benzoate, phenyl benzoate or benzyl benzoate, or also of an alkylbenzene such as trimethylbenzene or ethylbenzene, (G) 0.5 to 5% by weight of a salt of a $C_{10}$–$C_{24}$ fatty acid and a polyvalent metal, for example magnesium distearate, calcium dibehenate or aluminium tristearate, and (H) 0.5 to 3% by weight of a $C_1$–$C_4$ alkylenediamide of a fatty acid containing 10 to 24 carbon atoms, for example methylenebis(stearamide), ethylenebis(stearamide) or ethylenebis(behenamide).

Further preferred aqueous preparations comprise, based on the entire formulation, (a) 15 to 50% by weight of a nonionic polyadduct of styrene oxide with a polyalkylene glycol ether of formula (1), preferably a styrene oxide polyadduct of formula (4), (b) 1 to 5% by weight of an acid ester or salt thereof, for example an alkali metal or ammonium salt, of a compound of formula

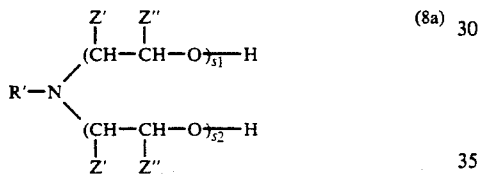

(8a)

or of its N-quaternised polyadduct of the acid ester or salt thereof, wherein R' is an alkyl or alkenyl radical of 12 to 22 carbon atoms, one of Z' and Z" is hydrogen, methyl or phenyl and the other is hydrogen, and $s_1$ and $s_2$ are each integers such that the sum of $s_1+s_2$ is 2 to 100, (c) 2 to 10% by weight of a quaternary ammonium compound of formula

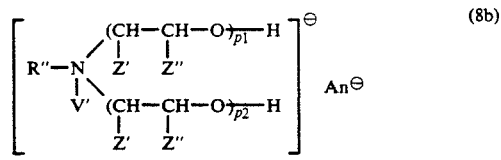

(8b)

wherein R" is an alkyl or alkenyl radical of 12 to 22 carbon atoms, V' is substituted or unsubstituted alkyl radical, such as methyl, ethyl, benzyl or —$CH_2CONH_2$, one of Z' and Z" is hydrogen, methyl or phenyl and the other is hydrogen, An$^\ominus$ is an anion of an inorganic or organic acid, and $p_1$ and $p_2$ are each integers such that the sum of $p_1$ and $p_2$ is from 2 to 100, with one or more of the following additional optional components:

(d) 0.5 to 25% by weight of a polyalkylene glycol ether of the formula

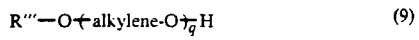

(9)

wherein R''' is an alkyl or alkenyl radical of 4 to 22 carbon atoms, "alkylene" is ethylene or propylene, and q is from 2 to 85, and (e) 0.5 to 5% by weight of a nitrogen-containing nonionic compound of formula

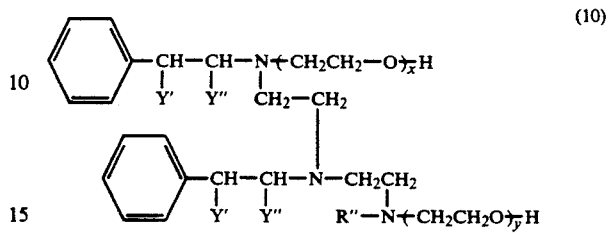

(10)

wherein R" is an alkyl or alkenyl radical of 12 to 22 carbon atoms, one of Y' and Y" is phenyl and the other is hydrogen, and x and y are each integers such that the sum of x and y is from 80 to 140.

Further details and preferred combinations and formulations of components (b), (c), (d) and (e) may be found in DE-A-1 568 258, DE-A-1 619 385, EP-A-89004 and EP-A-312493.

In the Preparatory and Use Examples below, percentages and parts are by weight, unless otherwise stated. Amounts of dye are based on commercial, i.e. diluted product, and amounts of auxiliaries are based on pure substance.

PREPARATORY EXAMPLES

EXAMPLE 1 a) 421.2 g of benzyl alcohol and 2.1 g of boron trifluoride etherate are heated together to 50° C. Then 300 g of styrene oxide are added dropwise over 60 minutes, the temperature rising to 85° C. The reaction mixture is further stirred for 15 minutes at 85° C. and excess benzyl alcohol is removed by distillation. Fractional distillation in a high vacuum gives 202 g of a colourless compound of formula

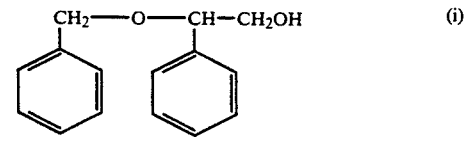

(i)

b.p.$_{10-2}$: 119°–122° C.; OH number: 230 b) 243.5 g of benzyloxyphenyl ethanol of formula (i) are reacted with 88 g of ethylene oxide in the presence of 1% of sodium methylate at 140° C. and a pressure of 2 bar, to give a compound of formula

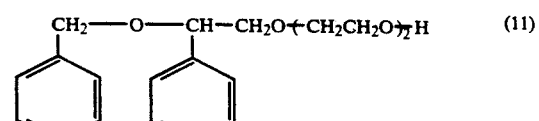

(11)

OH number: 180 c) 51 g of the adduct of formula (11) are heated to 60° C. and stirred for 15 minutes with 17.2 g of urea. Then 17.2 g of sulfamic acid are added and the reaction mixture is heated to 70° C., stirred for 1 hour at 70° C., heated to 95° C., and stirred for a further 2 hours at 95° C. Upon addition of 85.4 g of water a 50% clear solution of the compound of formula

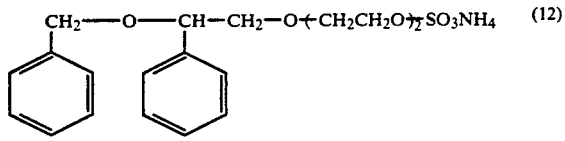

is obtained.

EXAMPLE 2

51 g of the adduct of formula (11) and 16.2 g of maleic anhydride are heated together to 70° C. The reaction mixture is then stirred for 1 hour at 70° C., the temperature is raised to 90° C., and stirring is continued for a further 3 hours at 90° C. A clear, viscous polyadduct of formula

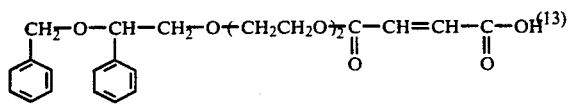

is obtained. The acid number is 144.

EXAMPLE 3

With stirring, 51 g of the adduct of formula (11) are mixed at room temperature with 7.8 g of phosphorus pentoxide, the temperature rising to 72° C. The mixture is subsequently stirred for 4 hours at room temperature to give a viscous mixture of phosphoric acid esters of formulae

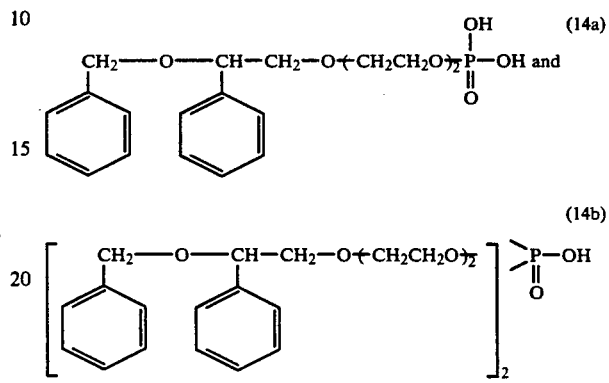

In a manner similar to that described in Examples 1 to 3, the following nonionic and anionic polyadducts are prepared using the appropriate starting materials:

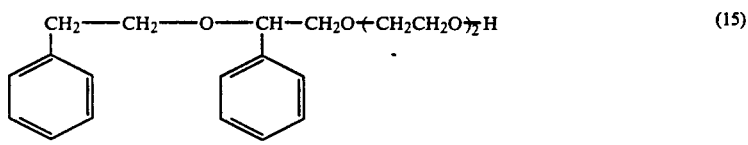

OH number: 188

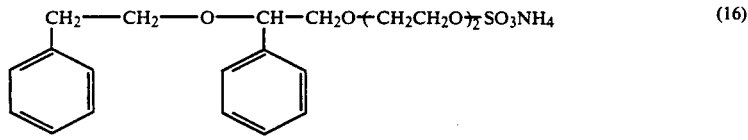

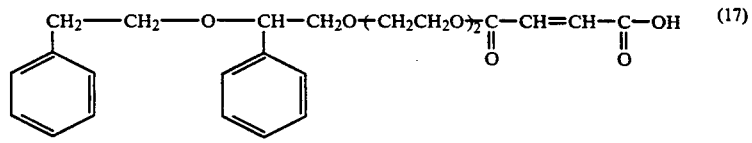

acid number: 156 mixture of a phosphoric acid monoester and diester of formulae (18a) and (18b)

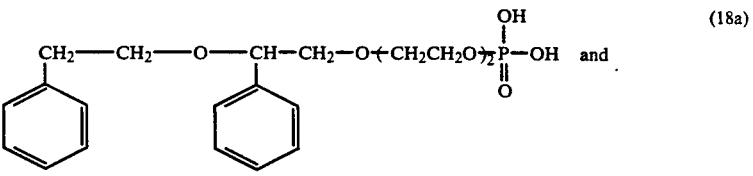

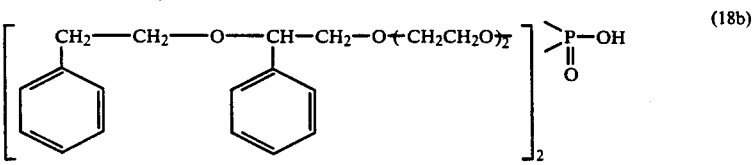

-continued

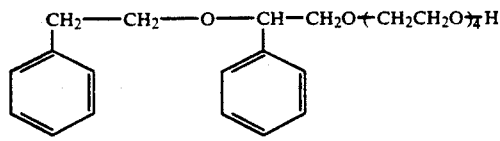

OH number: 159

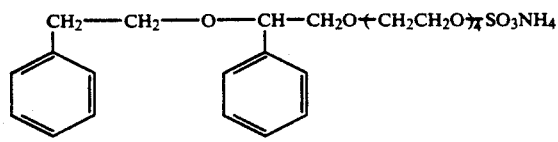

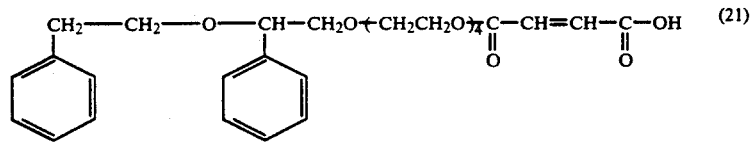

acid number: 124 mixture of a phosphoric acid monoester and diester of formulae (22a) and (22b)

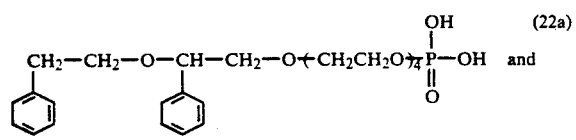

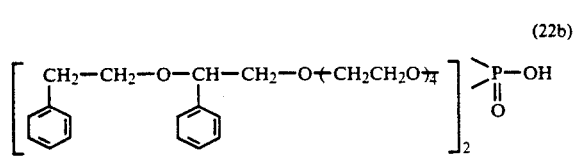

USE EXAMPLES

EXAMPLE 4

100 g of wool serge are wetted out in a circulating liquor machine at 40° C. for 15 minutes in a liquor comprising 1.1 liter of water and the following ingredients:
3.2 g of 80% acetic acid
5.0 g of calcined sodium sulfate
1 g of the adduct of formula (11).

Then 5 g of the dye Acid Black 172 C.I. 15 711 are added. After 10 minutes the dye liquor is heated to 85° C. over 45 minutes and the goods are kept for 60 minutes at this temperature with constant circulation. The dyebath is completely exhausted (dye on to the fibre). The dyed goods are then rinsed and dried. A deep, level black dyeing of the wool is obtained without conventional heating to boiling temperature. The fastness properties match those of a dyeing obtained at boiling temperature.

EXAMPLE 5

100 kg of wool in cheese form on a material carrier are put into a circulating dyeing machine. In the stock container, 1200 l of water are heated to 60° C. and 1200 g of an aqueous formulation which, based on said formulation, contains
12% of silicone oil, for example dimethyl polysiloxane
15% of 2-ethyl-n-hexanol
15% of paraffin oil
2% of a water-soluble, surface-active siloxaneoxyalkylene copolymer
8% of the anionic polyadduct of formula (13) and
2% of the nonionic polyadduct of formula (11)
and which has been adjusted to pH 8 with monoethanolamine, are dissolved therein. The liquor is then pumped from the stock container through the material into the dyeing machine with subsequent alternating circulation. The addition of the formulation effects spontaneous deaeration of the system and hence good penetration of the goods.

To the liquor are then added 2 kg of the dye of formula

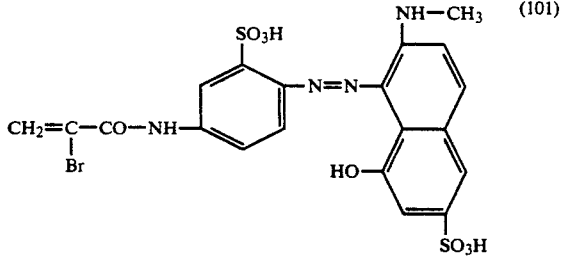

1 kg of a 1:1 mixture of the polyadduct of 7 mol of ethylene oxide with 1 mol of a $C_{16}$-$C_{18}$ fatty acid mixture, quaternised with chloroacetamide, and the ammonium salt of the sulfated polyadduct of 7 mol of ethylene oxide with 1 mol of a $C_{16}$-$C_{18}$ fatty acid mixture (50% aqueous formulation). The dye liquor is heated over 30 minutes to the boil and the wool is dyed for 60 minutes at boiling temperature. Virtually no foaming occurs during dyeing. A strong and level dyeing of the cheese is obtained.

The formulation used in this Example is prepared as follows:

12 parts of silicone oil are dissolved in 15 parts of 2-ethyl-n-hexanol. With continuous stirring, 15 parts of paraffin oil, 2 parts of a water-soluble, surface-active siloxaneoxyalkylene copolymer, 8 parts of the maleic monoester of formula (13), 2 parts of the polyadduct of formula (11), 47.6 parts of water and 0.4 part of monoethanolamine are then added, and the mixture is stirred for a further 30 minutes. A storage-stable formulation having a wetting, deaerating and, in particular, foam-inhibiting effect is obtained.

EXAMPLE 6

In a winch beck, 100 kg of cotton knitwear are wetted out in 3000 l of water containing 3 kg of an aqueous formulation containing, based on said formulation,
7% of a silicone oil
11% of 2-ethyl-n-hexanol and
11% of the anionic polyadduct of formula (12).
The cotton is completely wetted and deaerated within 30 seconds. To the liquor are added 2 kg of a dye of formula

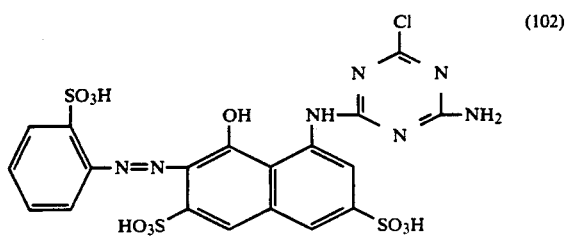

(102)

together with customary chemicals such as electrolytes and alkalis, and the knitwear is then dyed at the boil for two hours. No troublesome foaming occurs. A complete, level non-spotty dyeing is obtained.

The formulation used in the Example is prepared as follows:

70 parts of silicone oil are dissolved in 110 parts of 2-ethyl-n-hexanol at room temperature. Then 110 parts of the polyadduct of formula (12) are added, followed 30 minutes later by the addition of 710 parts of water, and thereafter the mixture is stirred for a further 30 minutes. A storage-stable formulation having excellent wetting and deaerating properties is obtained.

EXAMPLE 7

In a short liquor jet dyeing apparatus, 100 kg of cotton tricot are wetted out in 600 liters of water at 40° C. To the liquor are added 36 kg of sodium chloride, 5 kg of the dye of formula (102) and 0.5 kg of a formulation containing

| | |
|---|---|
| 186.75 | g of mineral oil (for example Shell Oil L 6189), |
| 185 | g of bis-2-ethylhexyl maleate, |
| 10 | g of magnesium distearate, |
| 8.25 | g of N,N-ethylenebis(stearamide), |
| 55 | g of a polyoxyethylene derivative of sorbitan tristearate with 20 oxyethylene units, e.g. Tween 65, and |
| 55 | g of the anionic polyadduct of formula (12). |

The goods are dyed at 40° C. for 45 minutes. Then 0.6 kg of calcined sodium carbonate is added, followed after a further 5 minutes by the addition of 1.2 kg of aqueous 36% sodium hydroxide solution. The tricot is then dyed for a further 40 minutes, and then rinsed and washed. A fast, level red dyeing is obtained on the tricot. During the dyeing process no foaming occurs and the passage of the goods is trouble-free.

The formulation used in this Example is prepared as follows:

186.75 g of mineral oil, 185 g of bis-2-ethylhexyl maleate, 10 g of magnesium distearate and 8.25 g of N,N-ethylenebis(stearamide) are heated, with continuous stirring, at 110° C. until a clear solution is obtained. The solution is cooled to 45° C. over 5 minutes, and 55 g of a polyoxyethylene derivative of sorbitan tristearate with 20 oxyethylene units, e.g. Tween 65, and 55 g of the anionic polyadduct of formula (12) are dispersed therein. The resultant stable formulation is in particular a very effective antifoam in alkaline liquors and at high shearing rates.

EXAMPLE 8

100 parts of polyester fabric are put into a hot dyeing liquor of 60° C. containing 1300 parts of water, 2 g/l of ammonium sulfate, 2.5 parts of a dye of formula

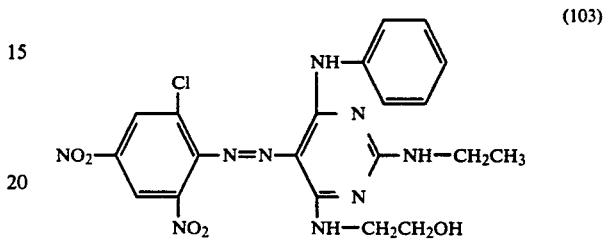

(103)

and 2 parts of an assistant formulation consisting of
16 parts of the anionic polyadduct of formula (13),
24 parts of the polyadduct of 18 mol of ethylene oxide with 1 mol of a $C_{12}$–$C_{18}$ fatty alcohol mixture and
60 parts of benzyl benzoate
and which has been adjusted to pH 5 with formic acid. The temperature of the liquor is raised to 130° C. over 30 minutes and dyeing is carried out at this temperature for 60 minutes.

The liquor is then cooled to 70° C., and dropped, and the polyester fabric is rinsed. Even without the customary reduction clearing a level and rub-fast red dyeing with a high colour yield is obtained.

The assistant formulation used in this Example is prepared as follows:

In a heatable stirred vessel, 60 parts of benzyl benzoate are heated to 60° C. with continuous stirring, and 24 parts of the polyadduct of 18 mol of ethylene oxide with 1 mol of a $C_{12}$–$C_{18}$ fatty alcohol mixture and 16 parts of the polyadduct of formula (13) are then stirred in. After cooling to room temperature a storage-stable formulation which is particularly suitable for dyeing polyester fibres is obtained.

EXAMPLE 9

100 parts of textured polyester yarns in package form are put into an HT dyeing machine which contains 800 parts of warm water of 40° C., 2 parts of ammonium sulfate, 4 parts of a dye of formula

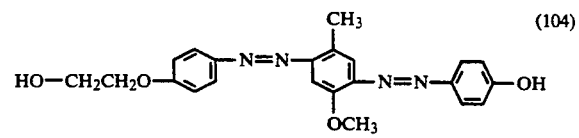

(104)

and 2 parts of the assistant formulation of Example 8 and whose liquor has been adjusted to pH 5.5 with formic acid. The temperature of the liquor is then raised to 128° C. over 40 minutes, and the goods are dyed at this temperature for 60 minutes. During the heating-up phase no increase in the differential pressure between the inside and the outside of the yarn package is detectable. Thereafter the liquor is cooled to 70° C., and the substrate is reduction cleared in conventional manner, rinsed and dried. A strong and level orange dyeing which is distinguished by good penetration and good fastness properties is obtained.

EXAMPLE 10

A nylon 6.6 loop pile carpet is impregnated on a padder at 25° C. with a formulation which contains, per liter, 1.2 g of a dye of formula

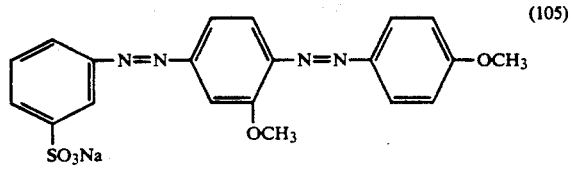
(105)

0.8 g of a dye of formula

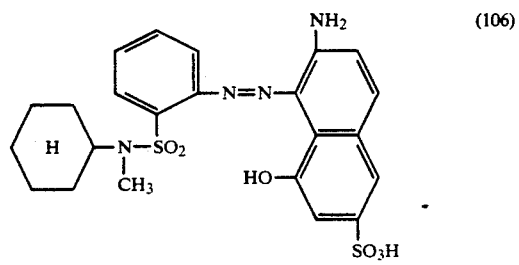
(106)

0.8 g of a dye of formula

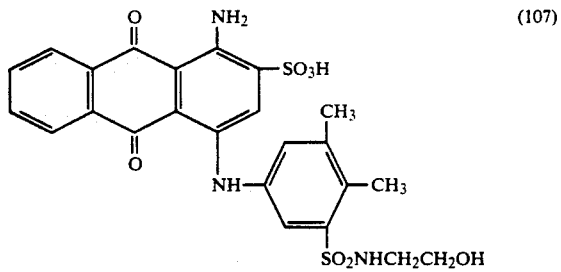
(107)

5 g of the polyadduct of formula (12) prepared as described in Example 1(c)

2 g of a thickener and 1 g of sodium acetate and which has been adjusted with acetic acid to pH 5–5.5. The liquor pick-up is 320%. The impregnated carpet is steamed with saturated steam in a dog house steamer at 100° C. for 5 minutes. The carpet is then rinsed with cold water and dried. A deep brown dyeing, without frosting and having the expected fastness properties is obtained.

EXAMPLE 11

100 g of wool serge are wetted out in a circulating liquor machine, for example an Ahiba-turbomat, at 40° C. for 15 minutes with a liquor comprising 1.1 liters of water containing the following ingredients:

3.2 g of 80% acetic acid 5 g of calcined sodium sulfate 2 g of an aqueous formulation containing, based on said formulation, 30% by weight of the styrene oxide polyadduct of formula (11), 10% by weight of the assistant mixture $A_1$ described in EP-A-0089004 and 20% by weight of triethylene glycol monobutyl ether.

4 g of the dye Acid Black 172 C.I. 15711 are then added. After 10 minutes, the dyeing liquor is heated to 90° C. over 50 minutes, and the goods are kept at this temperature with continuous circulation for 60 minutes. The goods are subsequently rinsed and dried.

A deep, level and fast black dyeing on the wool is obtained. The dye bath is 95% exhausted, although the dyeing was carried out at 90° C. The fastness properties match those of a conventional dyeing at the boil (98° C.).

What is claimed is:

1. An aqueous or non-aqueous formulation which comprises, based on the entire formulation,
   (A) 2 to 50% by weight of a maleic, malonic, succinic, sulfosuccinic, sulfuric or orthophosphoric acid ester of a compound of formula

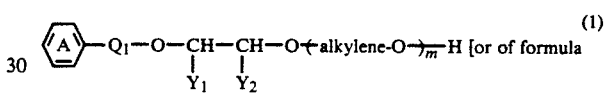
(1)

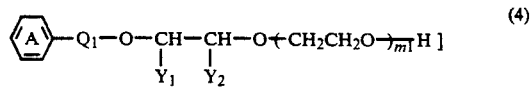
(4)

wherein the ring A is an unsubstituted phenyl radical or a phenyl radical which is substituted by halogen, methyl or $C_1$-$C_3$alkoxy, $Q_1$ is alkylene of 1 to 4 carbon atoms, one of $Y_1$ or $Y_2$ is phenyl and the other is hydrogen, "alkylene" denotes an alkylene radical of 2 or 3 carbon atoms, and m is an integer from 1 to 80, (B) 5 to 50% by weight of a nonionic surfactant and at least one of the following components:

(C) 1 to 30% by weight of a silicone oil, (D) 10 to 60% by weight of a mineral oil, (E) in addition to component (A), 20 to 45% by weight of a dialkyl ester of an ethylenically unsaturated aliphatic dicarboxylic acid (F) 10 to 70% by weight of an aliphatic or aromatic carboxylic acid ester or of an alkylbenzene, (G) 0.5 to 5% by weight of a salt of a $C_{10}$-$C_{24}$fatty acid and a polyvalent metal and (H) 0.5 to 3% by weight of a $C_1$-$C_4$alkylenediamide of a fatty acid of 10 to 24 carbon atoms.

2. A formulation according to claim 1, wherein $Q_1$, in formula (1), is methylene.

* * * * *